US009937175B2

(12) United States Patent
VanDeusen

(10) Patent No.: US 9,937,175 B2
(45) Date of Patent: *Apr. 10, 2018

(54) PHENYLOXADIAZOLE DERIVATIVES AS PGDS INHIBITORS

(71) Applicant: Sanofi, Paris (FR)

(72) Inventor: Christopher L. VanDeusen, East Windsor, NJ (US)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/258,892

(22) Filed: Sep. 7, 2016

(65) Prior Publication Data

US 2017/0231990 A1 Aug. 17, 2017

Related U.S. Application Data

(63) Continuation of application No. 13/439,511, filed on Apr. 4, 2012, now Pat. No. 9,469,627, which is a continuation of application No. PCT/US2010/051727, filed on Oct. 7, 2010.

(60) Provisional application No. 61/249,693, filed on Oct. 8, 2009.

(30) Foreign Application Priority Data

Jul. 26, 2010 (FR) ...................... 10 56094

(51) Int. Cl.
A61K 31/506 (2006.01)
C07D 217/06 (2006.01)
C07D 413/14 (2006.01)

(52) U.S. Cl.
CPC .......... *A61K 31/506* (2013.01); *C07D 217/06* (2013.01); *C07D 413/14* (2013.01)

(58) Field of Classification Search
CPC ... C07D 271/06; C07D 413/14; A61K 31/506
USPC .......................................... 544/333; 514/256
See application file for complete search history.

(56) References Cited

U.S. PATENT DOCUMENTS

| 5,176,132 | A | 1/1993 | Drought et al. |
| 7,951,956 | B2 | 5/2011 | Urade et al. |
| 8,202,863 | B2 | 6/2012 | Aldous et al. |
| 8,258,130 | B2 | 9/2012 | Aldous et al. |
| 9,469,627 | B2 | 10/2016 | Vandeusen et al. |
| 2004/0220411 | A1 | 11/2004 | Mederski et al. |
| 2008/0146569 | A1 | 6/2008 | Blake et al. |
| 2008/0207651 | A1 | 8/2008 | Blake |
| 2012/0190695 | A1 | 7/2012 | Vandeusen et al. |

FOREIGN PATENT DOCUMENTS

| CN | 1927860 A | 3/2007 |
| DE | 101 17 823 A1 | 10/2002 |
| JP | 2007-002220 | 1/2007 |
| JP | 2007-51121 A | 3/2007 |
| WO | WO 2002/083630 A1 | 10/2002 |
| WO | WO 2004/016223 A2 | 2/2004 |
| WO | WO 2004/026380 A2 | 4/2004 |
| WO | WO 2005/094805 A1 | 10/2005 |
| WO | WO 2007/007778 A1 | 1/2007 |
| WO | WO 2007/039177 | 4/2007 |
| WO | WO 2007/041634 A1 | 4/2007 |
| WO | WO 2008/121670 | 10/2008 |
| WO | WO 2008/122787 A1 | 10/2008 |
| WO | WO 2010/080563 A2 | 7/2010 |
| WO | WO 2011/044307 | 4/2011 |

OTHER PUBLICATIONS

Adeyeye, Moji, ed., Preformulation in Solid Dosage Form Development (Informa Healthcare, 2008) Chapter 2.3, pp. 63-80.
Bastin et al., Organic Process Research & Development 2000, 4, 427-435.
Berge, et al., Pharmaceutical Salts, J. Pharmaceutical Sciences, (1977), vol. 66, No. 1, pp. 1-19.
Brightling, et al., New Insights Into the Role of the Mast Cell in Asthma, Clin. Exp. Allergy, (2003), vol. 33, pp. 550-556.
Cheng, et al., Antagonism of the Prostaglandin D2 Receptor 1 Suppresses Nicotinic Acid-Induced Vasodilation in Mice and Humans, PNAS, vol. 103, No. 17, pp. 6682-6687, (2006).
Fujitani, et al., Pronounced Eosinophilic Lung Inflammation and Th2 Cytokine Release in Human Lipocalin-Type Prostaglandin D Synthase Transgenic Mice, Journal of Immunology, vol. 168, pp. 443-449, (2002).
Gould, Salt selection for basic drugs. International J. of Therapeutics 33: 201-213 & 217 (1986).
Ikai, et al., Inhibitory Effect of Tranilast on Prostaglandin D Synthetase, Biochemical Pharmacology, vol. 38, No. 16, pp. 2673-2676, (1989).
International Preliminary Report on Patentability and Written Opinion for PCT/US2010/051727, dated Apr. 11, 2012.

(Continued)

*Primary Examiner* — Deepak R Rao
(74) *Attorney, Agent, or Firm* — Cooley LLP

(57) ABSTRACT

This invention is directed to a compound of formula (I):

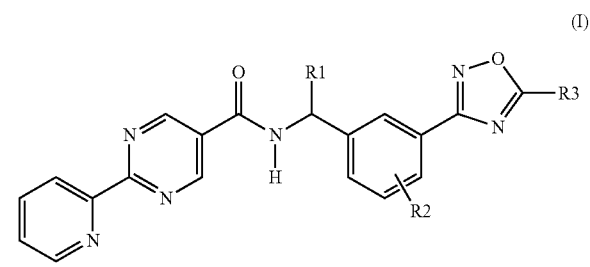

wherein R1, R2 and R3 are as defined herein, a pharmaceutical composition comprising the compound, intermediates and processes for making said compounds, and the use of the compound to treat allergic and/or inflammatory disorders, particularly disorders such as allergic rhinitis, asthma, chronic obstructive pulmonary disease (COPD) and age-related macular degeneration (AMD).

8 Claims, No Drawings

(56) References Cited

OTHER PUBLICATIONS

International Search Report for PCT/US1010/051727, dated Nov. 30, 2010.
Lewis, et al., Prostaglandin D2 Generation After Activation of Rat and Human Mast Cells With Anti-IgE, The Journal of Immunology, (1982), vol. 129, No. 4, pp. 1627-1631.
Liu, Rong, ed., Water-Insoluble Drug Formulation (CRC Press, 2008) Chapter 15 pp. 417-435.
Matsushita, et al., Pharmacological Studies on the Novel Antiallergic Drug HQL-79: II. Elucidation of Mechanisms for Antiallergic and Antiasthmatic Effects, Jpn. J. Pharmacol., vol. 78, pp. 11-22, (1978).
Mesquita-Santos, et al., Cutting Edge: Prostaglandin D2 Enhances Leukotriene C4 Synthesis by Eosinophils During Allegeric Inflammation: Synergistic In Vivo Role of Endogenous Eotaxin, J. Immunol, (2006), vol. 176, pp. 1326-1330.
Mohri, et al., Inhibition of Prostaglandin D Synthase Suppresses Muscular Necrosis, The American Journal of Pathology, vol. 174, No. 5, (2009), pp. 1735-1744.
Mohri, et al., Prostaglandin D2-Mediated Microglia/Astrocyte Interaction Enhances Astrogliosis and Demyelination in Twitcher, The Journal of Neuroscience, (2006), pp. 4383-4393, vol. 26, No. 16.
Morris, et al., International Journal of Pharmaceutics 105 (1994) 209-217.
Murray, et al., Release of Prostaglandin D2 Into Human Airways During Acute Antigen Challenge, The New England Journal of Medicine, (1986), vol. 315, No. 13, pp. 800-804.
Samadfam, et al., Implication of Prostaglandin Receptors in the Accumulation of Osteoprotegerin in Human Osteoblast Cultures, The Journal of Rheumatology, vol. 33, No. 6, pp. 1167-1175, (2006).
Serajuddin, Abu TM. "Salt formation to improve drug solubility." Advanced Drug Delivery Reviews 59.7 (2007): 603-616.
Stahl et al., eds., Handbook of pharmaceutical salts. Properties, selection and use (Wiley-VCH, 2008), pp. 265-327.
Swarbrick et al., eds. Encyclopedia of Pharmaceutical Technology 13 (Marcel Dekker, NY 1996) pp. 453-499.
Urade, et al., Prostaglandin D Synthase: Structure and Function, Vitamins and Hormones, vol. 58, pp. 89-120. (2000).
Yoshikawa, et al., Urinary PGDS Levels are Associated With Vascular Injury in Type 2 Diabetes Patients, Diabetes Research and Clinical Practice, vol. 76, (2007), pp. 358-267.

PHENYLOXADIAZOLE DERIVATIVES AS PGDS INHIBITORS

RELATED APPLICATIONS

This application is a continuation of U.S. application Ser. No. 13/439,511, filed Apr. 4, 2012, which is a continuation of International Application No. PCT/US2010/051727, filed Oct. 7, 2010, which claims priority to U.S. Provisional Application Ser. No. 61/249,693 filed Oct. 8, 2009, and French Patent Application No. 1056094 filed Jul. 26, 2010, the contents of all of which are incorporated herein in their entirety.

FIELD OF THE INVENTION

The present invention is directed to phenyloxadiazole compounds, their preparation, pharmaceutical compositions containing these compounds, and their pharmaceutical use in the treatment of disease states capable of being modulated by the inhibition of the prostaglandin D synthase.

BACKGROUND OF THE INVENTION

Allergic rhinitis, the most common atopic disease, has an estimated prevalence ranging from about 5 to about 22 percent of the general human population and is characterized by the symptoms of sneezing, nasal discharge, and nasal congestion. These symptoms are believed to be triggered by multiple mediators released from mast cells and other inflammatory cells. Current therapies, such as antihistamines, deal effectively with the sneezing and nasal discharge, but have little effect on congestion, which is a key symptom affecting the quality of life of patients.

Local allergen challenge in patients with allergic rhinitis, bronchial asthma, allergic conjunctivitis and atopic dermatitis has been shown to result in rapid elevation of prostaglandin D2 "(PGD2)" levels in nasal and bronchial lavage fluids, tears and skin chamber fluids. PGD2 has many inflammatory actions, such as increasing vascular permeability in the conjunctiva and skin, increasing nasal airway resistance, airway narrowing and eosinophil infiltration into the conjunctiva and trachea. PGD2 is the major cyclooxygenase product of arachidonic acid produced from mast cells on immunological challenge [Lewis, R A, Soter N A, Diamond P T, Austen K F, Oates J A, Roberts L J II, Prostaglandin D2 generation after activation of rat and human mast cells with anti-IgE, *J. Immunol.* 129, 1627-1631, 1982]. Activated mast cells, a major source of PGD2, are one of the key players in driving the allergic response in conditions such as asthma, allergic rhinitis, allergic conjunctivitis, allergic dermatitis and other diseases [Brightling C E, Bradding P, Pavord I D, Wardlaw A J, New Insights into the role of the mast cell in asthma, *Clin. Exp. Allergy* 33, 550-556, 2003].

In the presence of sulfhydryl compounds, PGD2 is formed by the isomerization of PGH2, a common precursor of prostanoids, by catalytic action of prostaglandin D synthase "(PGDS)". There are two isoforms of the PGDS enzyme: L-PGDS; and H-PGDS. H-PGDS is a cytosolic enzyme, which is distributed in the peripheral tissues, and which is localized in the antigen-presenting cells, mast cells, megakaryocytes, and Th2 lymphocytes. The action of the product PGD2 is mediated by G-protein coupled receptors: D prostaglandin "(DP)" and crTH2. See (1) Prostaglandin D Synthase: Structure and Function. T. Urade and O. Hayaishi, *Vitamin and Hormones,* 2000, 58, 89-120, (2) J. J. Murray, *N. Engl. J. Med.,* 1986 Sep. 25; 315(13):800, and (3) Urade et. al., *J. Immunology* 168: 443-449, 2002.

Without wishing to be bound by theory, inhibiting the formation of PGD2 should have an effect on nasal congestion and, therefore, be of therapeutic benefit in allergic rhinitis. In addition, we believe that a PGDS inhibitor should be of therapeutic benefit in a number of other indications such as bronchial asthma, age-related macular degeneration (AMD) an/or or chronic obstructive pulmonary disease (COPD).

Age-related macular degeneration (AMD) is a degenerative and progressive ocular disease that results in loss of fine, central vision due to the degeneration of the macula. AMD is the most common cause of blindness in Europe and the United States for individuals over 50 years of age.

Chronic obstructive pulmonary disease (COPD) is a progressive, inflammatory disease that involves chronic bronchitis and emphysema. Symptoms include airflow limitation, excessive mucus production, coughing, reduced exercise capacity and reduced quality of life.

PGDS inhibitors have been reported. The compound, HQL-79, is reported to be a weak PGDS inhibitor, and is antiasthmatic in guinea pig and rat models (Matsusshita, et al., Jpn. J. Pharamcol. 78: 11, 1998). The compound Tranilast is described as a PGDS inhibitor. (Inhibitory Effect of Tranilast on Prostaglandin D Synthesase. K. Ikai, M. Jihara, K. Fujii, and Y. Urade. Biochemical Pharmacology, 1989, 28, 2773-2676). The following published patent applications also disclose PGDS inhibitors:
US2008/0207651A1 and US2008/0146569A1—pyridine and pyrimidine carboxamides;
JP2007-51121—pyrimidine carboxamides;
WO2007/007778—benzimidazole derivatives;
WO2008/122787—piperazine(thio)carboxamides; and
WO2005/094805—imine and amide derivatives.

SUMMARY OF THE INVENTION

The present invention is directed to a compound of formula (I):

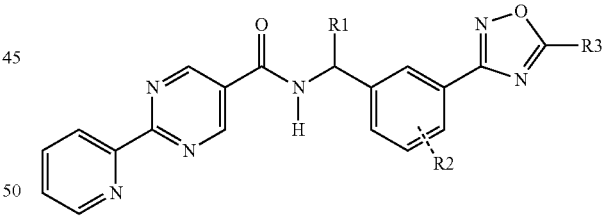

wherein:
R1 is hydrogen or $C_1$-$C_6$alkyl;
R2 is hydrogen, halogen or $C_1$-$C_3$alkyl; and
R3 is hydroxyalkyl
or a pharmaceutically acceptable salt thereof.

Another aspect of the present invention is a pharmaceutical composition comprising a pharmaceutically effective amount of a compound according to formula (I) and a pharmaceutically acceptable carrier.

Another aspect of the present invention is directed to a method of treating allergic and/or inflammatory disorders, particularly disorders such as allergic rhinitis, asthma, chronic obstructive pulmonary disease (COPD) and/or age-related macular degeneration (AMD) in a patient in need thereof by administering to the patient a compound according to formula (I). Another aspect of the invention is a process for preparing compounds of formula (I).

DETAILED DESCRIPTION OF THE INVENTION

Definition of Terms

As used above, and throughout the description of the invention, the following terms unless otherwise indicated, shall be understood to have the following meanings:

"Alkyl" means straight or branched aliphatic hydrocarbon having 1 to about 20 carbon atoms. Particular alkyl has 1 to about 12 carbon atoms. More particular alkyl is lower alkyl. Branched means that one or more lower alkyl groups such as methyl, ethyl or propyl are attached to a linear alkyl chain. "Lower alkyl" means 1 to about 4 carbon atoms in a linear alkyl chain that may be straight or branched.

"Hydroxyalkyl" means OH-alkyl-. Particular hydroxyalkyl is hydroxy($C_1$-$C_6$)alkyl-. Exemplary hydroxyalkyl includes 1-hydroxy-1-methyl-ethyl.

"Compounds of the present invention", and equivalent expressions, are meant to embrace compounds of Formula (I) as hereinbefore described. Reference to intermediates, whether or not they themselves are claimed, is meant to embrace their salts, N-oxides and solvates, where the context so permits.

"Halo" or "halogen" means fluoro, chloro, bromo, or iodo. Particular halo or halogen is fluoro or chloro.

"Patient" includes human and other mammals.

"Pharmaceutically acceptable salts" refers to the non-toxic, inorganic and organic acid addition salts, and base addition salts, of compounds of the present invention. These salts may be prepared in situ during the final isolation and purification of the compounds or by separately reacting the purified compound in its free base form with a suitable organic or inorganic acid and isolating the salt thus formed. In some cases, the compounds themselves are capable of self-protonating basic sites on the molecule and forming an internal amphoteric salt.

"Suitable couple reagent" refers to a reagent suitable for reacting an amine with a carboxylic acid. Suitable coupling reagents include, but are not limited to, DMTMM, carbonyldiimidazole (CDI) and TBTU, DCC, phosphonium salts, and uronium salts.

Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts. See, for example S. M. Berge, et al., "Pharmaceutical Salts," *J. Pharm. Sci.*, 66, 1-19 (1977) that is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. A particular base addition salt is sodium salt or potassium salt. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and particularly include those amines which are frequently used in medicinal chemistry because of their low toxicity and acceptability for medical use. Ammonia, ethylenediamine, N-methyl-glucamine, lysine, arginine, ornithine, choline, N,N'-dibenzyl-ethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabictylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine.

A particular embodiment of the invention is a compound of formula (I) wherein:

R1 is hydrogen;
R2 is hydrogen; and
R3 is hydroxyalkyl;
or a pharmaceutically acceptable salt thereof.

Another particular embodiment of the invention is a compound of formula (I) wherein:

R1 is $C_1$-$C_6$alkyl;
R2 is hydrogen; and
R3 is hydroxyalkyl;
or a pharmaceutically acceptable salt thereof.

Another particular embodiment of the invention is a compound of formula (I), which is:

2-Pyridin-2-yl-pyrimidine-5-carboxylic acid 3-5-(1-hydroxy-1 methyl-ethyl)[1,2,4]oxadiazol-3-yl]benzyl amide;

2-Pyridin-2-yl-pyrimidine-5-carboxylic acid ((S)-1-{3-[5-(1-hydroxy-1-methyl-ethyl)-1,2,4-oxadiazol-3-yl]-phenyl}-ethyl)-amide; or 2-Pyridin-2-yl-pyrimidine-5-carboxylic acid ((R)-1-{3-[5-(1-hydroxy-1-methyl-ethyl)-1,2,4-oxadiazol-3-yl]-phenyl}-ethyl)-amide;

or a pharmaceutically acceptable salt thereof.

It is to be understood that this invention covers all appropriate combinations of the particular embodiments referred thereto.

The present invention also includes within its scope a pharmaceutical composition comprising a pharmaceutically effective amount of a compound of the invention, in admixture with a pharmaceutically acceptable carrier.

Compounds of the present invention are PGDS inhibitors and thus, are useful for treating allergic and/or inflammatory disorders, particularly disorders such as allergic rhinitis, asthma, chronic obstructive pulmonary disease (COPD), chronic rhinosinusitus (CRS), and age-related macular degeneration (AMD). Accordingly, another invention herein is directed to a method of treating a patient suffering from allergic rhinitis, asthma, chronic obstructive pulmonary disease (COPD) and/or age-related macular degeneration (AMD) comprising administering to the patient a pharmaceutically effective amount of compound of formula (I).

In addition to the indications and disorders recited above, PGDS inhibitors, including compounds of formula I, are useful for the treatment of PGD2 mediated diseases including DP1, DP2, TP & PPAR gamma associated diseases. Such diseases and disorders include the following:

1) Skin diseases including atopic dermatitis, chronic urticaria, flushing Proc Natl Acad Sci U.S.A. 2006 Apr. 25; 103(17):6682-7);
2) Allergic diseases of the digestive system such as eosinophilic eosophagitis;
3) Neurodegenerative diseases such as Alzheimer's and Krabbes disease (The Journal of Neuroscience, Apr. 19, 2006, 26(16):4383-4393);
4) Muscle diseases such as Duchenne Muscular Dystrophy and Polymyositis (*American Journal of Pathology.* 2009; 174:1735-1744);
5) Conditions associated with increased eosinophils or Eosinophilic Syndrome;
6) Diseases of the eye such as Uveitis, Graves Ophthalmopathy, allergic conjunctivitis and glaucoma;
7) Vascular injury associated with diabetes such as diabetic retinopathy or with metabolic syndrome (Diabetes Res Clin Pract. 2007 June; 76(3):358-67); and
8) Bone diseases such as rheumatoid arthritis and osteoarthritis (J Rheumatol 2006; 33:1167-75).

References herein directed to treating should be understood to include prophylactic therapy to inhibit PGDS, as well as to treat an established acute or chronic or physiological conditions associated with PGDS to essentially cure a patient suffering therefrom, or ameliorate the physiological conditions associated therewith. Physiological conditions discussed herein include some, but not all, of the possible clinical situations where an anti-allergic rhinitis and/or asthma treatment is warranted. Those experienced in this field are well aware of the circumstances requiring treatment.

In practice, the compound of the present invention may be administered in pharmaceutically acceptable dosage form to humans and other mammals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the particular route may vary with for example the physiological condition of the recipient.

"Pharmaceutically acceptable dosage forms" refers to dosage forms of the compound of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for the compound of the invention to be administered in the form of a pharmaceutical composition.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride, and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates. Exemplary lubricants include magnesium stearate, sodium lauryl sulfate, talc, as well as high molecular weight polyethylene glycols.

The choice of pharmaceutical acceptable carrier is generally determined in accordance with the chemical properties of the active compound such as solubility, the particular mode of administration and the provisions to be observed in pharmaceutical practice.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of the compound of the invention is solid form, for example capsules, tablets, pills, powders, dragées or granules. In such solid dosage forms, the compound of the invention is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k)

buffering agents, and agents which release the compound of the invention in a certain part of the intestinal tract in a delayed manner.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compound can be microencapsulated in, or attached to, a slow release or targeted delivery systems such as a biocompatible, biodegradable polymer matrices (e.g., poly(d,l-lactide coglycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria-retaining filter, or by incorporating sterilizing agents in the form of sterile solid compositions that can be dissolved in sterile water, or some other sterile injectable medium immediately before use.

"Liquid dosage form" means the dose of the active compound to be administered to the patient is in liquid form, for example, pharmaceutically acceptable emulsions, solutions, suspensions, syrups and elixirs. In addition to the active compound, the liquid dosage forms may contain inert diluents commonly used in the art, such solvents, solubilizing agents and emulsifiers.

When aqueous suspensions are used they can contain emulsifying agents or agents which facilitate suspension.

Pharmaceutical compositions suitable for topical administration mean formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients, in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with, or without, stabilizer(s) make up the emulsifying wax, and together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as, propylene glycol, butane 1,3-diol, mannitol, sorbitol, glycerol and polyethylene glycol (including PEG 400) and mixtures thereof. The topical formulations may desirably include a compound that enhances absorption, or penetration of the active ingredient through the skin, or other affected areas.

The choice of suitable oils or fats for a composition is based on achieving the desired properties. Thus a cream should particularly be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations mean formulations that are in a form suitable to be administered rectally or vaginally to a patient and containing at least one compound of the invention. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical composition administered by injection may be by transmuscular, intravenous, intraperitoneal, and/or subcutaneous injection. The compositions of the present invention are formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

Pharmaceutical composition of the present invention suitable for nasal or inhalational administration means compositions that are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Inhalational therapy is readily administered by metered dose inhalers or any suitable dry powder inhaler, such as the Eclipse, Spinhaler®, or Ultrahaler® as described in patent application WO2004/026380, and U.S. Pat. No. 5,176,132.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

Total daily dose of the compound of this invention administered to a patient in single or divided doses may be in amounts, for example, of from about 0.001 to about 100 mg/kg body weight daily and particularly 0.01 to 10 mg/kg/day. For example, in an adult, the doses are generally from about 0.01 to about 100, particularly about 0.01 to about 10, mg/kg body weight per day by inhalation, from about 0.01 to about 100, particularly 0.1 to 70, more especially 0.5 to 10, mg/kg body weight per day by oral administration, and from about 0.01 to about 50, particularly 0.01 to 10, mg/kg body weight per day by intravenous administration.

The percentage of active ingredient in a composition may be varied, though it should constitute a proportion such that a suitable dosage shall be obtained. Dosage unit compositions may contain such amounts or such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much lower maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the pharmaceutically active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds of the invention may be prepared by the application or adaptation of known methods, by which is a meant method used heretofore or described in the literature, for example those described by R.C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T.W. Greene and P. G. M. Wuts, *Protecting Groups in Organic Synthesis*, 3rd edition, John Wiley & Sons, Inc., 1999.

A compound of formula (I) may be prepared (as shown in Scheme I below) by reacting a amine of type XI with a pyridylpyrimidinyl carboxylic acid (preparation shown in Scheme II) in the presence of a dehydrating coupling reagent, such as DMTMM, in a variety of solvents including but not limited to DMF. Suitable couple reagents include, but are not limited to, DMTMM, carbonyldiimidazole (CDI) and TBTU, DCC, phosphonium salts, and uronium salts. A compound of formula (I) may also be prepared (as shown in Scheme Ia below) by direct coupling of an amine of type XI with a pyridylpyrimidinyl ester (preparation shown in Scheme II) in the presence of 0.1 to 1.0 equivalents of 1,5,7-triazabicyclo[4.4.0]dec-5-ene (TBD). The reaction can be performed in the absence of solvent, or in the presence of added solvents, including, but not limited to ethers, esters, aromatic hydrocarbons. The use of strong bases other than TBD, including, but not limited to DBU and tetramethyl guanidine, also give product. The amine XI may be prepared through a process as detailed in Scheme III. A benzylic bromide VII may be reacted with Di-tert-butyl iminodicarboxylate in the presence of bases including but not limited to cesium carbonate in a variety of solvents including but not limited to DMF to yield compounds VIII. These compounds of type VIII may then be reacted with hydroxylamine (in the presence of bases including but not limited to triethylamine in the cases where salts of hydroxylamine are used, such as hydroxylamine hydrochloride) in a variety of solvents including but not limited to methanol to yield an amidoxime IX. The amidoxime may be reacted with a compound containing a carboxy functionality including but not limited to a methyl carboxylate in the presence of a base including but not limited to potassium carbonate either in the presence or absence of a solvent including but not limited to toluene (in certain cases the carboxy functionality may serve as a solvent for the reaction) to yield an oxadiazole X. The oxadiazole X may then be exposed to acidic conditions including but not limited to hydrogen chloride in methanol to yield an amine XI. In the cases where R1 alkyl substitution is desired in amine XI, these amines may be prepared according to Scheme IV (either in enantioenriched or racemic form) using the tert-butyl sulfinamide methodology developed by Ellman.

Scheme I
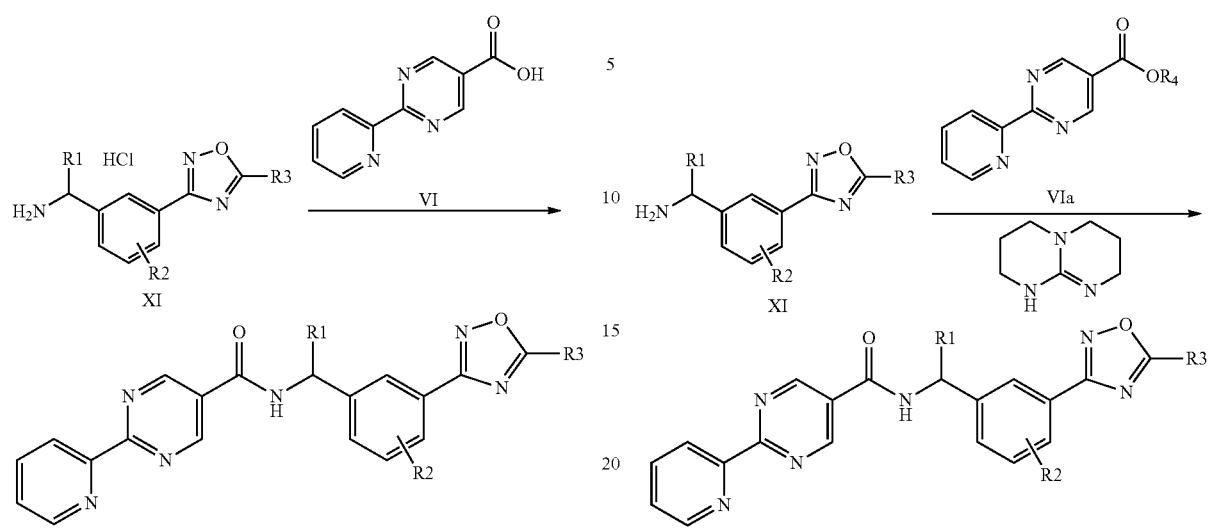
wherein R1, R2 and R3 are as defined in formula (I)
Scheme Ia
wherein R1, R2 and R3 are as defined in formula (I) and R4 is $C_1$-$C_3$alkyl
Scheme II
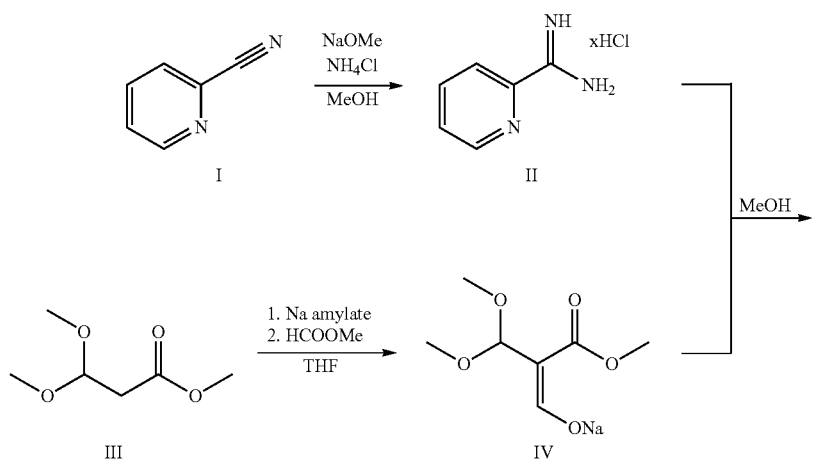
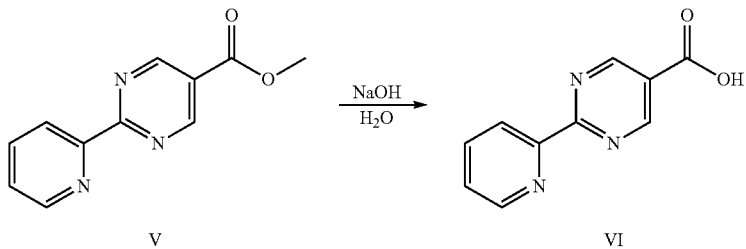

Scheme III

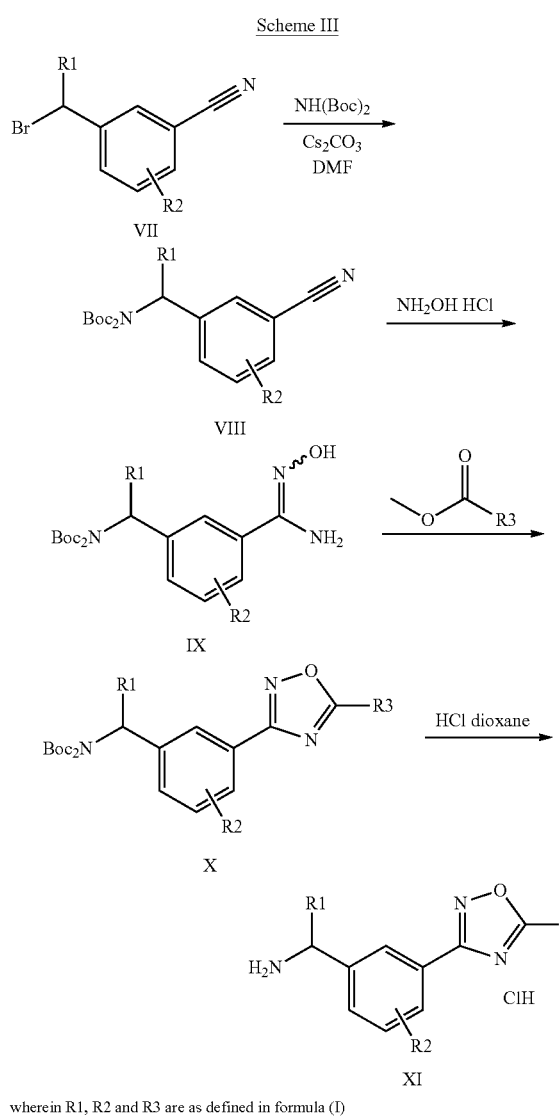

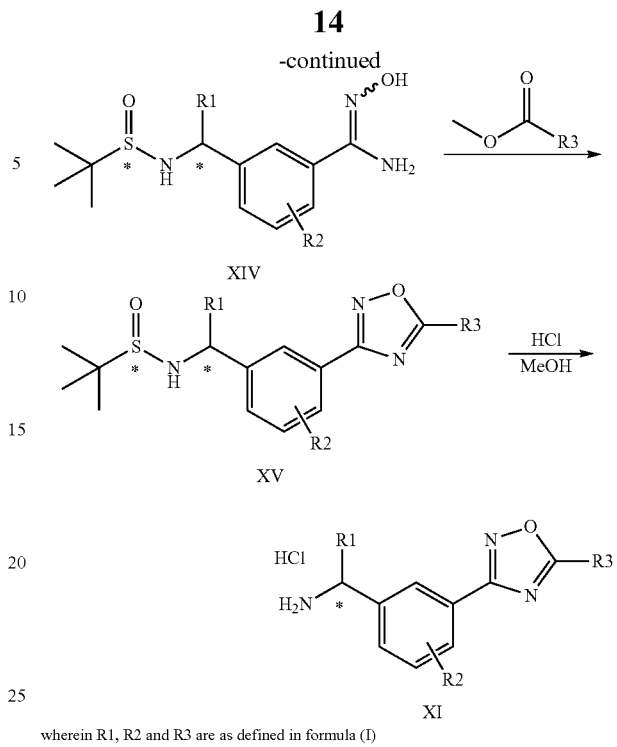

wherein R1, R2 and R3 are as defined in formula (I)

Scheme IV

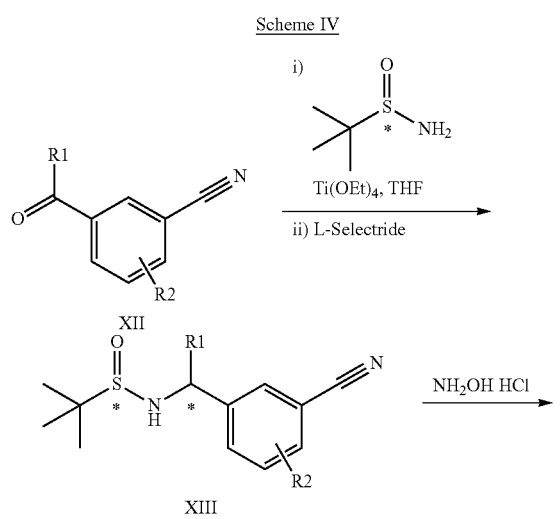

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallization techniques, or they are separately prepared from the appropriate isomers of their intermediates.

The compounds of the invention, their methods or preparation and their biological activity will appear more clearly from the examination of the following examples that are presented as an illustration only and are not to be considered as limiting the invention in its scope. Compounds of the invention are identified, for example, by the following analytical methods.

Mass Spectra (MS) are recorded using a Micromass LCT mass spectrometer. The method is positive electrospray ionization, scanning mass m/z from 100 to 1000.

300 MHz $^1$H nuclear magnetic resonance spectra ($^1$H NMR) are recorded at ambient temperature using a Varian Mercury (300 MHz) spectrometer with an ASW 5 mm probe. In the $^1$H NMR chemical shifts (δ) are indicated in parts per million (ppm) with reference to tetramethylsilane (TMS) as the internal standard.

As used in the examples and preparations that follow, as well as the rest of the application, the terms used therein shall have the meanings indicated: "kg"=kilograms, "g"=grams, "mg"=milligrams, "g"=micrograms, "mol"=moles, "mmol"=millimoles, "M"=molar, "mM"=millimolar, "M"=micromolar, "nM"=nanomolar, "L"=liters, "mL" or "ml"=milliliters, "L"=microliters, "° C."=degrees Celsius, "mp" or "m.p."=melting point, "bp" or "b.p."=boiling point, "mm of Hg"=pressure in millimeters of mercury, "cm"=centimeters, "nm"=nanometers, "abs."=absolute, "conc."=concentrated, "c"=concentration in g/mL, "rt"=room temperature, "TLC"=thin layer chromatography, "HPLC"=high performance liquid chromatography, "i.p."=intraperitoneally, "i.v."=intravenously, "s"=singlet, "d"=doublet; "t"=triplet; "q"=quartet; "m"=multiplet, "dd"=doublet of doublets; "br"=broad, "LC"=liquid chromatograph, "MS"=mass spectrograph, "ESI/MS"=electrospray ionization/mass spectrograph, "$R_T$"=retention time, "M"=molecular ion, "PSI"=pounds per square inch, "DMSO"=dimethyl sulfoxide, "DMF"=N,N-dimethylformamide, "DCM"=dichloromethane, "HCl"=hydrochloric acid, "SPA"=Scintillation Proximity Assay, "EtOAc"=ethyl acetate, "PBS"=Phosphate Buffered Saline, "IUPAC"=International Union of Pure and Applied Chemistry, "MHz"=megahertz, "MeOH"=methanol, "N"=normality. "THF"=tetrahydrofuran. "min"=minute(s), "$N_2$"=nitrogen gas, "MeCN" or "$CH_3CN$"=acetonitrile, "$Et_2O$"=ethyl ether, "TFA"=trifluoroacetic acid, "~"=approximately, "$MgSO_4$"=magnesium sulfate, "$Na_2SO_4$"=sodium sulfate, "$NaHCO_3$"=sodium bicarbonate, "$Na_2CO_3$"=sodium carbonate, "MCPBA"=3-Chloroperoxybenzoic acid, "NMP"=N-methylpyrrolidone, "PS-DCC"=polymer supported-dicyclohexylcarbodiimide, "LiOH"=Lithium hydroxide, "PS-trisamine"=polymer supported-trisamine, "PGH2"=prostaglandin H2, "PGD2"=prostaglandin D2; "PGE2"=prostaglandin E2, "hPGDS"=Hematopoietic PGD2 Synthase, "GSH"=glutathione (reduced), "EIA"=Enzyme immunoassay, "$KH_2PO_4$"=potassium phosphate, monobasic, "$K_2HPO_4$"=potassium phosphate, dibasic, "$FeCl_2$"=ferrous chloride, "MOX"=methoxyamine; "EtOH"=ethanol, "DMSO"=dimethylsulfoxide, "$Ag_2O$"=silver(I) oxide, "HATU"=O-(7-azabenzotriazole-1-yl)-N,N,N',N'-tetramethyluronium hexafluorophosphate, "HOAt"=1-hydroxy-7-azabenzotriazole, "DIPEA"=N,N-diisopropylethylamine, "HOTT"=S-(1-Oxido-2-pyridyl)-N,N,N',N'-tetramethylthiuronium hexafluorophosphate, "HCTU"=N,N,N',N'-tetramethyl-O-(6-chloro-1H-benzotriazol-1-yl)uronium hexafluorophosphate, "PyBrOP"=bromo-tris-pyrrolidinophosphonium hexafluorophosphate, "LiAlH4"=lithium aluminum hydride, "PyAOP"=(7-azabenzotriazol-1-yloxy)-tripyrrolidinophosphonium hexafluorophosphate, "TBTU"=O-benzotriazol-1-yl-N,N,N,N,-tetramethyluronium tetrafluoroborate, "NaHMDS"=sodium bis(trimethylsilyl)amide, "NMP"=N-methyl-2-pyrrolidinone, "HOSA"=hydroxylamine-O-sulfonic acid, "DMTMM"=4-(4,6-dimethoxy-1,3,5-triazin-2-yl)-4-methylmorpholinium chloride, "$TMSN_3$"=trimethylsilyl azide, "TBAF"=tetrabutylammonium fluoride, "TFAA"=trifluoro acetic anhydride.

EXAMPLES

Following procedures similar to those described in the above examples, the following compounds are made:

Example 1

2-Pyridin-2-yl-pyrimidine-5-carboxylic acid 3-[5-(1-hydroxy-1-methyl-ethyl)-1,2,4-oxadiazol-3-yl]-benzylamide

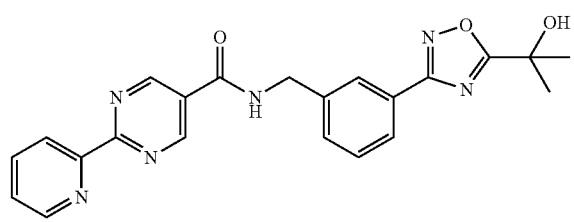 [SMILES: CC(C)(O)c1nc(-c2cccc(CNC(=O)c3cnc(-c4ccccn4)nc3)c2)no1]

Step 1

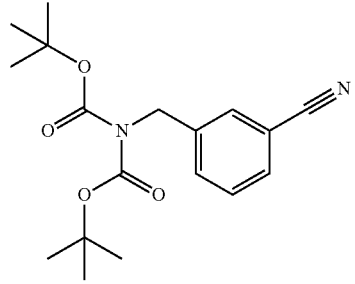 [SMILES: CC(C)(C)OC(=O)N(Cc1cccc(C#N)c1)C(=O)OC(C)(C)C]

3-Bromomethyl-benzonitrile (42.9 g, 219 mmol, 1 equivalent) is combined with Di-tert-butyl iminodicarboxylate (50 g, 230.13 mmol, 1.05 equivalents) and cesium carbonate (74.98 g, 230.13 mmol, 1.05 equivalents) in N,N-dimethyl formamide (DMF) (230 mL). The reaction is stirred at room temperature overnight and then partitioned between diethyl ether (500 mL) and water (1 L). The aqueous layer is extracted with an additional portion of diethyl ether (250 mL) and the combined ether layers are washed with brine (2×200 mL). The organic layer is then dried ($MgSO_4$), filtered, and reduced in vacuo to yield oil that slowly crystallized to give 2-[(3-cyanophenyl)methyl]-imidodicarbonic acid 1,3-bis(1,1-dimethylethyl) ester (72 g, 99%).

MS: 333 (M+H), 355 (M+Na).

$^1$H NMR (300 MHz, $CDCl_3$): δ=1.47 (s, 18H), 4.79 (s, 2H), 7.42 (t, 1H), 7.54-7.60 (m, 3H).

Step 2

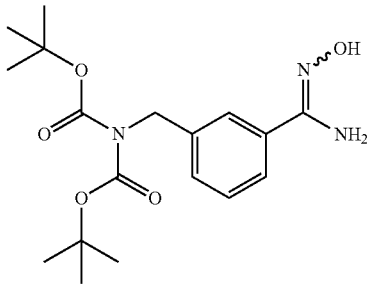 [SMILES: CC(C)(C)OC(=O)N(Cc1cccc(C(N)=NO)c1)C(=O)OC(C)(C)C]

Hydroxylamine hydrochloride (23.43 g, 375 mmol, 2.5 equivalents) is added to a solution of 2-[(3-cyanophenyl)methyl]-imidodicarbonic acid 1,3-bis(1,1-dimethylethyl) ester (50 g, 150 mmol, 1 equivalent) in methanol (450 mL) and the mixture is chilled in an ice water bath. Triethylamine (37.87 g, 375 mmol, 2.5 equivalents) is added and the reaction mixture is allowed to stir overnight, warming up to room temperature slowly as the bath thaws. The reaction is then reduced in vacuo and the residue partitioned between ethyl acetate (1 L) and water (500 mL). The water layer is extracted with an additional portion of ethyl acetate (200 mL) and the combined organic layers are washed with brine (200 mL), dried over sodium sulfate, and filtered. At this point, heptane and toluene (100 mL each) are added and the reaction reduced in vacuo to yield 2-[[3-[(hydroxyamino)iminomethyl]phenyl]methyl]-imidodicarbonic acid 1,3-bis(1,1-dimethylethyl) ester as a clear gel (54.7 g (>99%), that is used directly without further purification.

Step 3

Potassium carbonate (4.35 g, 31.46 mmol, 1.15 equivalents) is added to a flask charged with 2-[[3-[(hydroxyamino)iminomethyl]phenyl]methyl]-imidodicarbonic acid 1,3-bis(1,1-dimethylethyl) ester (10 g, 27.36 mmol, 1 equivalent) from step 2 in Toluene (30 mL), followed by 2-Hydroxy-2-methyl-propionic acid methyl ester (3.716 g, 31.46 mmol, 1.15 equivalents). The reaction is heated to reflux. After 48 hours the reaction is partitioned between EtOAc (300 mL) and water (200 mL). The EtOAc is washed with Brine (100 mL), dried over sodium sulfate, filtered and then reduced in vacuo to yield a residue that is taken on directly.

A solution of 4N HCl in dioxane (60 mL) is added to an ice chilled mixture of the residue (27 mmol) from the previous reaction in p-dioxane (60 mL). The ice water bath is removed and the reaction is allowed to warm to room temperature. After 6 hours, the reaction is diluted with diethyl ether (200 mL). The white solid is collected via filtration, washed with diethyl ether (~50 mL) and then dried in vacuo to yield 3-[5-(1-Hydroxy-1-methyl-ethyl)-[1,2,4]oxadiazol-3-yl]-benzyl-amine hydrochloride (5.84 g, 79% over two steps).

MS: 234 (M+H). $^1$H NMR (300 MHz, DMSO): δ=1.626 (s, 6H), 4.13-4.15 (d, 2H), 6.11 (bs, 1H), 7.62 (t, 1H), 7.72 (d, 1H), 8.02 (d, 1H), 8.15 (s, 1H), 8.45 (bs, 3H).

Step 4

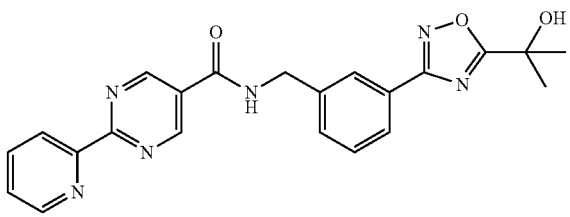 [SMILES: CC(C)(O)c1nc(-c2cccc(CNC(=O)c3cnc(-c4ccccn4)nc3)c2)no1]

N-methyl morpholine (NMM) (1.12 g, 11.12 mmol, 1 equivalent) is added to a mixture of 2-Pyridin-2-yl-pyrimidine-5-carboxylic acid (2.24 g, 11.12 mmol, 1 equivalent) and 3-[5-(1-Hydroxy-1-methyl-ethyl)-[1,2,4]oxadiazol-3-yl]-benzyl-amine hydrochloride (3 g, 11.12 mmol, 1 equivalent) in DMF (50 mL). After stirring at room temperature for 5 minutes, 4-(4,6-Dimethoxy-[1,3,5]triazin-2-yl)-4-methyl-morpholin-4-ium chloride (DMTMM) (3.08 g, 11.12 mmol, 1 equivalent) is added and the reaction stirred at room temperature, for 3 hours. The reaction is diluted into ice water (500 mL) and the suspension is extracted with EtOAc (2×300 mL). The combined ethyl acetate layers are washed with brine (2×100 mL), dried over sodium sulfate, and reduced in vacuo to give crude product which is recrystallized using ethyl acetate/ethanol to yield 2-Pyridin-2-yl-pyrimidine-5-carboxylic acid 3-[5-(1-hydroxy-1-methyl-ethyl)-1,2,4-oxadiazol-3-yl]-benzylamide as white crystalline solid (1.95 g, 42%) Note: Yields are variable depending on the purity of the coupling partners and solvents used for recrystallization. MS: 417 (M+H). $^1$H NMR (300 MHz, DMSO): δ=1.62 (s, 6H), 4.65 (d, 2H), 6.08 (s, 1H), 7.54-7.63 (m, 3H), 7.93 (d, 1H), 7.99-8.04 (m, 2H), 8.45 (d, 1H), 8.79 (d, 1H), 9.37 (s, 2H), 9.57 (t, 1H).

Alternatively, the coupling may be achieved using CDI (carbonyldiimidazole) or TBTU. The coupling shown below may be done in, for example, DMF and/or THF.

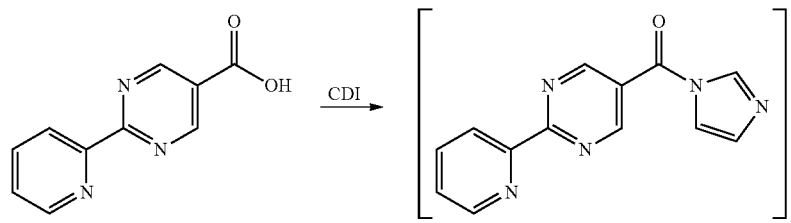

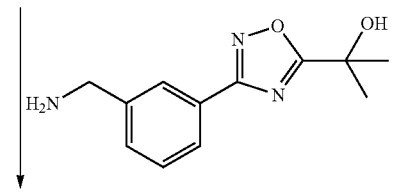

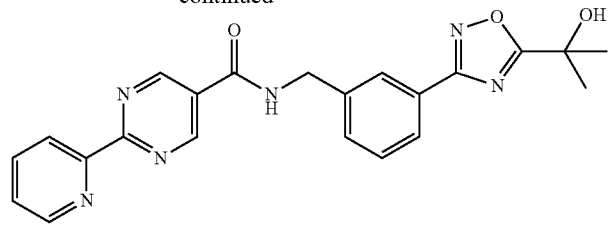

To a 5 L jacketed reactor was added 68.89 g of the carboxylic acid and about 346 ml DMF. To this slurry was added 74.9 g of the CDI at 22±2° C. The amine (79.87 g) was dissolved in about 69 mL DMF and added over 8 minutes. This turned the thick slurry into a clear yellow/brown solution. The temperature increased to 35° C. Heptane (202 ml) was added followed by water (596 ml) slowly over 20 minutes. During water addition, the temperature increased from 22 to 33° C. As the reaction mixture was stirred, crystals began to form. Water (5.15 L) was added. The reaction mixture was filtered on a 185 mm diameter Buchner and washed with 2×750 mL water. The cake was collected and dried under vacuum (45° C., 100 mbar pressure, nitrogen flush) to yield 122.15 g of product.

HPLC method: Eclipse XDB phenyl column, 3.5 micron, 4.6×150 mm, detection at 254 nm, gradient: started at 5:95:0.1% ACN/water/TFA then ramped over 8 min to 70:30:0.1% ACN/water/TFA, held 4.5 min; product retention time: 6.5 min.

Alternatively, the coupling may proceed via the acid chloride as shown below.

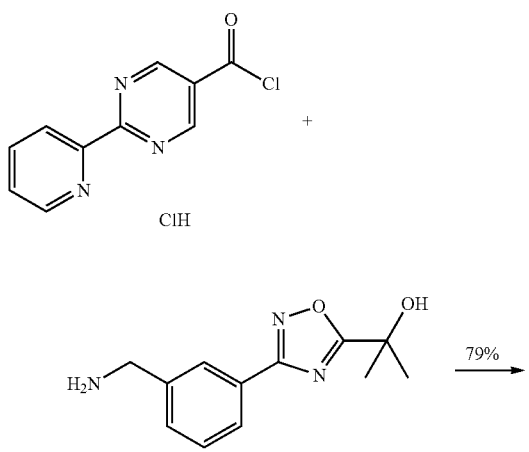

-continued

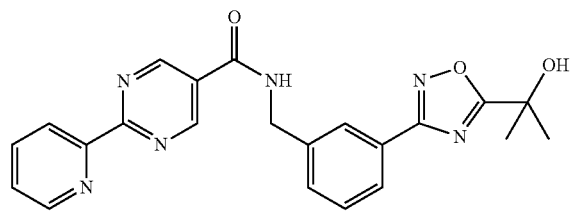

A 100 mL 3 neck round bottom flask equipped with magnetic stirring, temperature controller, and Firestone Valve (N2) was charged with 2-[3-(3-aminomethylphenyl)-[1,2,4]-oxadiazol-5-yl]-propan-2-ol free base (600 mg, 2.57 mmole, 1 eq), NMP (5 mL) and triethylamine (2.25 mL). 2-Pyridin-2-yl-pyrimidine-5-carbonyl chloride HCl (0.7 g, 2.7 mmole, ca 96% acid) was added. The reaction was quenched after about 2.5 hours by adding toluene (5 mL) and water (5×10 mL). The reaction was filtered and the cake was washed with toluene and water to yield a solid (0.85 g, 79% yield).

$^1$H NMR (300 MHz, d$_6$-DMSO): δ=1.61 (s, 6H), 4.64 (d, 2H), 6.08 (s, 1H), 7.6 (m, 3H), 7.95 (d, 1H), 8.04 (m, 2H), 8.45 (d, 1H), 8.8 (d, 1H), 9.37 (s, 1H), 9.57 (t, 1H)

Example 1a

Alternative synthesis for 3-[5-(1-Hydroxy-1-methyl-ethyl)-[1,2,4]oxadiazol-3-yl]-benzyl-amine hydrochloride

SCHEME V

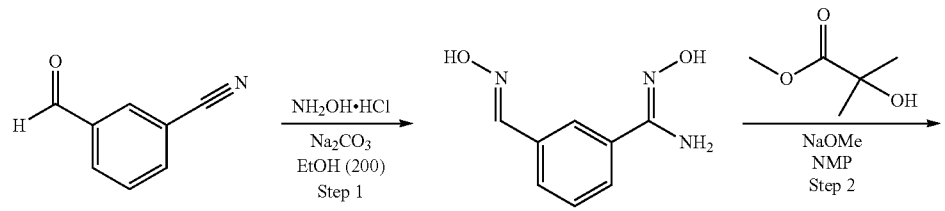

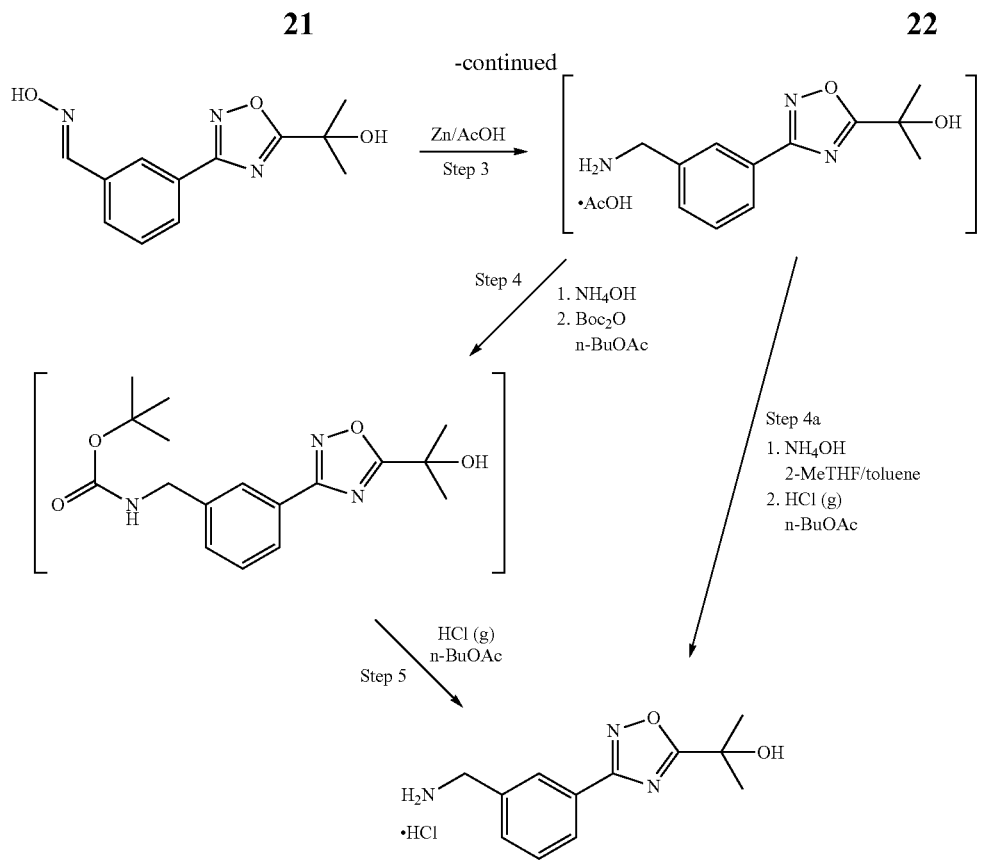

Scheme V—Step 1

A 5-L jacketed glass reactor equipped with an overhead mechanical stirrer, a thermocouple probe and a nitrogen purge was charged at 20-25° C. with 3-cyanobenzaldehyde (100.0 g, 0.763 mol, 1.0 eq.) and ethanol (200 proof) (394.5 g, 500 mL, 5 v/w parts). To the suspension was charged via addition funnel, a solution of hydroxylamine hydrochloride (159.0 g, 2.288 mole, 3.0 eq.) in water (250 mL, 2.5 parts) over a period of 30-45 min while maintaining temperature of 20-25° C. The addition funnel was rinsed with water (20 mL) and the rinse was added to the reactor. After addition of ca 45 mL of $NH_2OH.HCl$ solution, the solid dissolved to provide a clear solution. Within 10 min the solution turned cloudy and a solid crystallized to provide a suspension. The solid is believed to be the oxime resulting from addition of hydroxylamine to the aldehyde function. The suspension was stirred at 20-25° C. for 1 h. To the suspension was charged via a addition funnel, a solution of sodium carbonate (121.25 g, 1.144 mole, 1.5 eq,) in water (390 mL, 3.9 parts) over a period of 1.5-2.0 h while maintaining a temperature of 20-22° C. The addition funnel was rinsed with water (20 mL) and the rinse was added to the reactor. Evolution of $CO_2$ was observed. The suspension was heated to 29-30° C. and stirred at 29-30° C. for 24 h. Water (1.32 L, 13.2 parts) was charged to the reactor over 45-60 min while maintaining a temperature of 30-32° C. The suspension was heated to and held at 76-78° C. for 30-60 min to get a clear solution. The solution was cooled to 55-60° C. over 90 min. Product crystallized at 55-60° C. The suspension was stirred at 55-60° C. for 60 min. The suspension was cooled to 20-22° C. over 8-12 h. The suspension was cooled to 2-5° C. and stirred at 2-5° C. for 4 h. The suspension was filtered (Buchner funnel, 14.5 cm o.d.) and the cake was washed with water (250 mL, 2.5 parts). The cake was dried under suction for 5 h. The cake was transferred to a drying dish and dried under vacuum (25-50 torr, 50° C., $N_2$) for 60 h to provide 127.33 g (93.2% yield) of product as a white crystalline solid with a purity of 99.9% (HPLC).

HPLC Method: Zorbax Eclipse XDB C8 column, 5 micron, 4.6×150 mm, 25° C., detection at 240 nm, gradient: 5:95:0.1 $CH_3CN/H_2O$/TFA isocratic 2 min then ramped over 16 min to 90:10:0.1 $CH_3CN/H_2O$/TFA; product retention time: 3.6-4.4 min (three peaks)

Scheme V—Step 2

A 5-L jacketed glass reactor equipped with an overhead mechanical stirrer, a thermocouple probe and a nitrogen purge was charged at 22-27° C. with (N-hydroxy-3-hydroxyiminomethyl)benzamidine) (100.0 g, 0.558 mol, 1.0 eq.) and 1-methyl-2-pyrrolidinone (NMP) (267.3 g, 260 mL, 2.6 v/w parts). To the suspension was charged via addition funnel methyl 2-hydroxyisobutyrate (197.8 g, 1.674 mole, 3.0 eq.) over 15-30 min while maintaining temperature of 25-27° C. The mixture was stirred at 25-27° C. for 30-45 min to get a clear solution. To the solution was charged via an addition funnel 25 w % sodium methoxide solution in methanol (361.7 g, 1.674 mole, 3.0 eq.) over 30-60 min while maintaining a temperature of 25-27° C. The solution was heated at 29-30° C. for 7 hours. After 30-45 min at 29-30° C., the solution turned into a suspension. Water (1.8 L, 18 parts) was charged via an addition funnel over 30-60 min while maintaining a temperature of 22-25° C. The suspension dissolved to provide a clear solution with a pH 12.2 (pH meter). The pH of the solution was adjusted to 5.0 by charging hydrochloric acid (37.1 w %) (77.4 g, 0.787 mole, 1.4 eq) over 30-45 min while maintaining a temperature of 22-25° C. The product crystallized upon acidification with hydrochloric acid. After cooling to 5-10° C. and stirring at 5-10° C. for 2 h, the suspension was filtered (Buchner funnel, 27.5 cm i.d.), and the cake was washed with water (700 mL, 7 parts) and dried under suction for 7 h. The cake was transferred to a drying dish and dried under vacuum (25-50 torr, 50° C., N2) for 20-24 h to provide 132.0 g (95.6% yield) of product as a white crystalline solid with a purity of 99.7% (HPLC).

HPLC Method: Zorbax Eclipse XDB C8 column, 5 micron, 4.6×150 mm, 25° C., detection at 240 nm, gradient: 5:95:0.1 $CH_3CN/H_2O$/TFA isocratic 2 min then ramped over 16 min to 90:10:0.1 $CH_3CN/H_2O$/TFA; product retention time: 10.8 min Scheme V—Step 3

A 5-L jacketed glass reactor equipped with an overhead mechanical stirrer, a thermocouple probe and a nitrogen purge was charged at 20-25° C. with 3-[5-(1-hydroxy-1-methylethyl)-[1,2,4]oxadiazol-3-yl]benzaldehyde oxime (100.0 g, 0.404 mol, 1.0 eq.) and glacial acetic acid (1888.2 g, 1.8 L, 18 v/w parts). The suspension was heated to 28-30° C. and stirred till a clear solution was obtained (30-45 min). The solution was cooled to 22-24° C. and zinc dust (105.8 g, 1.618 mole, 4.0 eq.) was added via an addition funnel over 90-120 min while maintaining a temperature of 22-26° C. Note: Zinc dust addition was exothermic. The suspension was stirred at 24-26° C. for 2-3 hours. The suspension was filtered under $N_2$ (an inverted funnel with $N_2$ supply) through Celite (40 g). The solids were washed with EtOH (200 proof)/$H_2O$ (1/1, 894.5 g, 1 L, 10 parts) and EtOH (200 proof) (250 mL, 197.3 g, 2.5 parts). The filtrate was transferred to a 5-L reactor and concentrated under reduced pressure (45-50 torr, 44-47° C., jacket temperature 50-55° C.) to a volume of ca. 350 mL (3.5 parts). The vacuum was broken with $N_2$ and the reactor was cooled to 22° C. The mixture was a thick suspension. Toluene (2162.5 g, 2.5 L, 25 parts) was charged to the reactor and suspension was concentrated under reduced pressure (70-75 torr, 42-47° C., jacket temperature 50-55° C.) to a volume of ca 350 mL (3.5 parts). Vacuum was broken with $N_2$ and the reactor was charged with toluene (129.8 g, 150 mL, 1.5 parts) at 22° C. The suspension was stirred at 22° C. for 15-20 minutes and the phases were allowed to separate. The upper layer is mainly toluene and the lower layer contains the acetate salt of desired product.

HPLC Method: Zorbax Eclipse XDB C8 column, 5 micron, 4.6×150 mm, 25° C., detection at 240 nm, gradient: 5:95:0.1 $CH_3CN/H_2O$/TFA isocratic 2 min then ramped over 16 min to 90:10:0.1 $CH_3CN/H_2O$/TFA; product retention time: 7.9 min Scheme V—Step 4a 2-MeTHF (1290.0 g, 1.5 L, 15 parts) was added to the reactor. Aqueous ammonium hydroxide (29.5 w %) (353.8 g, 400 mL, 4 parts) was charged via an addition funnel over 30-45 min while maintaining a temperature of 20-25° C. The mixture was stirred at 22-25° C. for 30-45 min and the phases were allowed to separate. The pH of the aqueous phase should be basic (pH observed 10.9). The organic phase was washed with 15.3 w % aqueous sodium chloride (2×442.1 g, 2×400 mL, 2×4 parts). Note: 15.3 w % aq. NaCl was prepared by dissolving NaCl (180 g) in water (1000 g). The organic phase was concentrated under reduced pressure (100-110 torr, 30-34° C., jacket temperature 35-40° C.) to a volume of ca 900 mL (9 parts). Vacuum was broken with $N_2$ and the solution was filtered to remove a small amount of NaCl (ca 400 mg). The funnel was rinsed with 2-MeTHF (86.0 g, 100 mL, 1 part) to provide a solution of 2-[3-(3-aminomethylphenyl)-[1,2,4]-oxadiazol-5-yl]-propan-2-ol free base in 2-MeTHF/toluene (899.0 g, 1 L, 10 parts). Assay (w/w) of the solution provided the product (83.61 g, 9.3 w %) in 88.7% yield with a purity of 95.1 A % (HPLC); 2-MeTHF 68.7 w % and toluene 21.2 w %.

HPLC Method: Zorbax Eclipse XDB C8 column, 5 micron, 4.6×150 mm, 25° C., detection at 240 nm, gradient: 5:95:0.1 $CH_3CN/H_2O$/TFA isocratic 2 min then ramped over 16 min to 90:10:0.1 $CH_3CN/H_2O$/TFA; product retention time: 7.8 min Scheme V—Step 4

A 5 L reactor equipped with mechanical stirrer, thermocouple probe and N2 inlet was charged with THF (1.5 L) and 2-[3-(3-aminomethylphenyl)-[1,2,4]-oxadiazol-5-yl]-propan-2-ol AcOH (111.27 g). The solution turned into a suspension. A solution of $Na_2CO_3$ (85.73 g) in water (600 ml) was added slowly with cooling (thermocouple at 15° C.). The reaction was stirred at room temperature for about 10 minutes. Di-tert-butyl dicarbonate (97.1 g) in THF (90 mL) was added via a dropping funnel over about 12 minutes with cooling (thermocouple set to 15° C.). The reaction mixture was warmed (thermocouple set to 22° C.). The mixture separates into two distinct layers after first appearing as a suspension and then becomes a suspension again. Ethyl acetate (750 mL) was added and the suspension was stirred for 15 minutes at room temperature. Celite (545 (25 g) was added to the reactor and the mixture was stirred for 15 minutes. The slurry was transferred to a 4 L Erlenmeyer flask. It was filtered through Celite 545 (sintered glass funnel, Kimax 2000 mL-125° C. charged with 100 g of Celite 545). The Celite/zinc salts were washed with ethyl acetate (500 mL). The organic layer was collected and washed with 1/1 H2O/sat. aq NaCl (2×500 mL), pH of aqueous layer 5-7. The filtrate was charged to a clean reactor and the reactor was fitted with a one-piece distillation apparatus (P=250 torr, Δp=5 torr, thermocouple set to 40° C.). When the volume of liquid in reactor was about 250 mL, the pressure was equalized with N2 and the reaction was cooled (thermocouple set to 22° C.). The reactor was charged with ethyl acetate (1500 mL). Resumed distillation (P=180-200 torr, Δp=5 torr, thermocouple set to 50° C.) till volume of solution in the reactor was ca 500 mL. The pressure was equalized with N2 and the reaction was cooled (thermocouple set to 22° C.). Yield of {3-[5-(1-hydroxy-1-methylethyl)-[1,2,4]oxadiazol-3-yl]-benzyl-carbamic acid tert-butyl ester=126.46 g (quant., solution in ethyl acetate). The solution was used in step 5

HPLC Method: Zorbax Eclipse XDB C8 column, 5 micron, 4.6×150 mm, 25° C., detection at 240 nm, gradient: 5:95:0.1 $CH_3CN/H_2O$/TFA isocratic 2 min then ramped over 16 min to 90:10:0.1 $CH_3CN/H_2O$/TFA; product retention time: 13.8 min Scheme V—Step 5

A 5 L reactor equipped with a mechanical stirrer, thermocouple and N2 inlet was charged with {3-[5-(1-hydroxy-1-methylethyl)-[1,2,4]oxadiazol-3-yl]-benzyl-carbamic acid tert-butyl ester (126.46 g) as solution in ethyl acetate (from step 4). The solution was cooled (3-15° C.). Added HCl gas (102 g) from a lecture bottle over 30 minutes. The reaction was warmed to 15° C. over 45 minutes and a slurry was formed. This slurry was transferred to an Erlenmeyer flask (1 L). The contents were then filtered using a Buchner funnel. The cake was rinsed with ethyl acetate (350 mL) and suction dried. The solid was then transferred to a drying dish and dried (0.9" Hg, 35 C, N2) to yield 83.52 g of a solid (76.6% overall yield steps 3-5).

HPLC Method: Zorbax Eclipse XDB C8 column, 5 micron, 4.6×150 mm, 25° C., detection at 240 nm, gradient:

5:95:0.1 CH₃CN/H₂O/TFA isocratic 2 min then ramped over 16 min to 90:10:0.1 CH₃CN/H₂O/TFA; product retention time: 8.0 min Example 1b

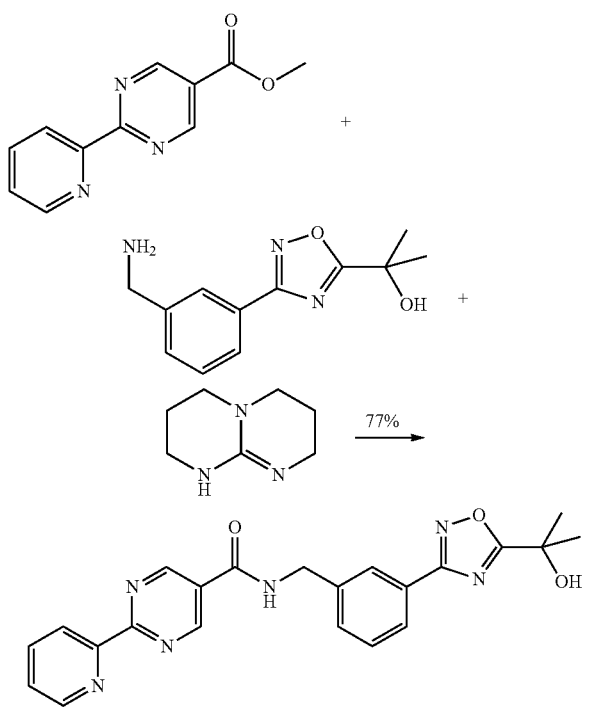

A reactor with stirring and a nitrogen blanket was charged with 2-Me-THF (5 mL), the ester (500 mg), the benzylamine (545 mg) and 1,5,7-triazabicyclo[4,4,0]dec-5-ene (TBD) (97.5 mg, 0.3 eq) to yield a yellowish suspension. The reactor was positioned into a heating block that was preheated to 79° C. The reaction was stirred for about 3 hours, then was removed from the block, allowed to cool to room temperature, then placed in an ice bath, stirred 15 minutes, and filtered. The reactor and cake were rinsed with 1 mL cold 2-Me-THF. The white caked was rinsed with 5×2 mL water at room temperature and suction dried for 1.5 hours. The white solid (0.77 g) was transferred to an oven and heated at 70° C. (N2, 45 mbar) overnight. Yield: 750 mg, 77%.

Alternative work up: After a reaction employing 2-Me-THF (4 mL), the ester (300 mg), the benzylamine (327 mg) and 1,5,7-triazabicyclo[4,4,0]dec-5-ene (TBD) (58.5 mg, 0.3 eq) was complete, the mixture was partitioned with 2 mL of water and cooled. The organic phase was separated, diluted with 2 mL of 2-Me-THF, then was washed with 5 mL of water. The combine aqueous phase was extracted with 2 mL of 2-Me-THF. The combined organic phase was concentrated and dried. Yield: 0.57 g, 97%.

HPLC method: Eclipse XDB C8 column, 5 micron, 4.6×150 mm, 35° C., detection at 270 nm, gradient: 5:95: 0.1% ACN/water/TFA held 5 min then ramped over 7 min to 50:50:0.1% ACN/water/TFA, held 3 min; product retention time: 12.9 min.

Example 2

2-Pyridine-2-yl-pyrimidine-5-carboxylic acid ((S)-1-{3-[5-(1-hydroxy-1-methyl-ethyl)-1,2,4-oxadiazol-3-yl]-phenyl}-ethyl)-amide

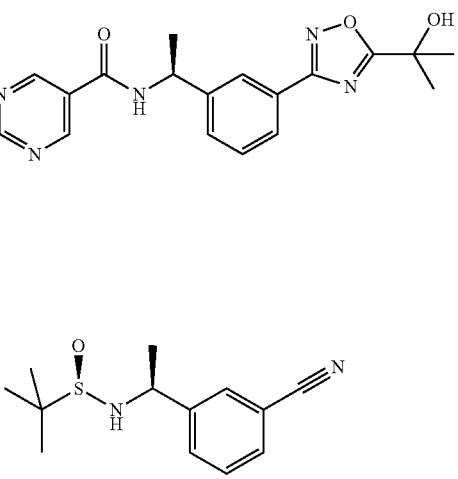

Step 1

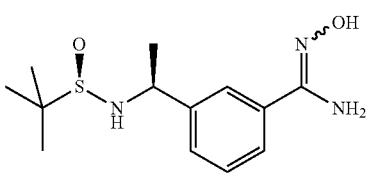

3-Acetylbenzonitrile (5 g, 34.4 mmol) is added to a flask containing (R)-(+)-2-Methyl-2-propanesulfinamide (3.48 g, 28.7 mmol) and titanium (IV) ethoxide (13.1 g, 57.4 mmol) in THF (70 mL) and the reaction mixture heated at 75° C. overnight. The reaction mixture is cooled (−48° C.) and L-Selectride (1M solution in THF, 57.4 mL) added dropwise over 1 hour. The reaction stirred for 2 hrs and allowed to warm to room temperature. The reaction is then cooled to 0° C. and methanol (3 mL) added. Brine (150 mL) is added with stirring and the suspension filtered through Celite. The crude material is extracted with ethyl acetate, dried (MgSO₄), filtered and evaporated under vacuum. The cruse is purified by column chromatography eluting with heptane-ethyl acetate to give N-[(1S)-1-(3-cyanophenyl)ethyl]-2-methyl-[S(R)]-2-propanesulfinamide (78%)

MS: 251 (M+H)

¹H NMR (300 MHz, CDCl₃): δ=1.22 (s, 9H), 1.54 (d, 3H), 3.36 (bs, 1H), 4.55-4.7 (m, 1H), 7.43 (d, 1H), 7.46 (d, 1H), 7.56-7.6 (m, 2H), 7.64 (s, 1H).

Step 2

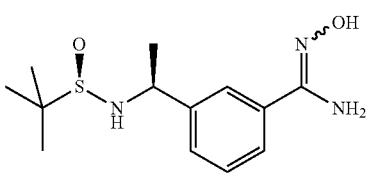

N-Hydroxy-3-[(S)-1-(2-methyl-propane-2-sulfinylamino)-ethyl]-benzamidine Hydroxylamine hydrochloride (3.43 g, 55 mmol) and methanol (70 mL) are added to a flask containing N-[(1S)-1-(3-cyanophenyl)ethyl]-2-methyl-[S(R)]-2-propanesulfinamide (5.5 g, 22 mmol) and the suspension cooled in an ice water bath. Triethyl amine (5.55 g, 55 mmol) is added to the flask and the reaction mixture is allowed to warm to room temperature over night. The reaction mixture evaporated under reduced pressure and the crude partitioned between water and DCM. Organic layer separated, dried (Na₂SO₄) and evaporated under reduced pressure to give N-Hydroxy-3-[(S)-1-(2-methyl-propane-2-sulfinylamino)-ethyl]-benzamidine (5.48 g).

MS: 284 (M+H). ¹H NMR (300 MHz, CDCl₃): δ=1.21 (s, 9H), 1.52 (s, 3H), 3.33 (s, 1H), 3.77 (bs, 1H), 4.59-4.61 (m, 1H), 4.88 (1H, bs), 7.35-7.37 (m, 2H), 7.50-7.52 (m, 1H), 7.64 (s, 1H)

Step 3

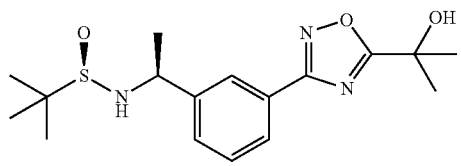

2-Methyl-propane-2-sulfinic acid ((S)-1-{3-[5-(1-hydroxy-1-methyl-ethyl)-1,2,4-oxadiazol-3-yl]-phenyl}-ethyl)-amide Methyl 2-Hydroxy-2-methyl-propionate (20 mL) and K₂CO₃ (806 mg, 5.8 mmol) are added to a flask containing N-Hydroxy-3-[(S)-1-(2-methyl-propane-2-sulfinylamino)-ethyl]-benzamidine (1.5 g, 5.3 mmol) and heated under reflux for 6 hrs. The reaction mixture is evaporated under reduced pressure and partitioned between water and ethyl acetate. The organic layer separated, dried (Na₂SO₄) and purified by flash column chromatography eluting with heptane-ethyl acetate mixture to give 2-Methyl-propane-2-sulfinic acid ((S)-1-{3-[5-(1-hydroxy-1-methyl-ethyl)-1,2,4-oxadiazol-3-yl]-phenyl}-ethyl)-amide (1.05 g).

MS: 352 (M+H). ¹H NMR (300 MHz, CDCl₃): δ=1.22 (s, 9H), 1.58 (d, 3H), 1.75 (s, 6H), 3.48 (bs, 1H), 4.65 (m, 1H), 7.45-7.47 (m, 2H), 8.01 (m, 1H), 8.08 (s, 1H)

Step 4

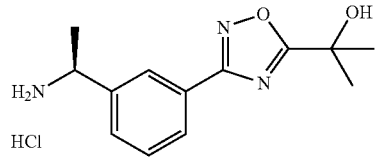 [SMILES: Cl ; C[C@H](N)c1cccc(-c2noc(C(C)(C)O)n2)c1]

2-{3-[3-((S)-1-Amino-ethyl)-phenyl]-1,2,4-oxadiazol-5-yl}-propan-2-ol Hydrochloride Hydrogen chloride in p-dioxane (4N, 1.42 mL) is added to a cooled solution of 2-Methyl-propane-2-sulfinic acid ((S)-1-{3-[5-(1-hydroxy-1-methyl-ethyl)-1,2,4-oxadiazol-3-yl]-phenyl}-ethyl)-amide (1 g, 2.85 mmol) in methanol (3 mL) at 0° C. and stirred for 20 min. Diethyl ether (30 mL) is added, decanted, and the residue is washed with another aliquot of diethyl ether. The residue is dried in vacuo to yield 2-{3-[3-((S)-1-Amino-ethyl)-phenyl]-1,2,4-oxadiazol-5-yl}-propan-2-ol Hydrochloride (560 mg).

MS: 231 (ES+, —OH ionized) ¹H NMR (300 MHz, DMSO): δ=1.55 (d, 3H), 1.63 (s, 6H), 4.53-4.57 (m, 1H), 6.1 (bs, 1H), 7.64 (t, 1H), 7.76 (d, 1H), 8.01 (d, 1H), 8.15 (s, 1H), 8.56 (bs, 2H)

Step 5

N-methyl morpholine (NMM) (196 mg, 1.94 mmol) is added to a mixture of 2-Pyridin-2-yl-pyrimidine-5-carboxylic acid (390 mg, 1.94 mmol) and 2-[3-[3-((S)-1-Amino-ethyl)-phenyl]-1,2,4-oxadiazol-5-yl]-propan-2-ol Hydrochloride (550 mg, 1.94 mmol) in DMF (20 mL). After stirring at room temperature for 5 minutes, 4-(4,6-Dimethoxy-[1,3,5]triazin-2-yl)-4-methyl-morpholin-4-ium chloride (DMTMM) (537 mg, 1.94 mmol) is added and the reaction stirred at room temperature for 2 hours. The reaction mixture poured on to ice water and the suspension is extracted with EtOAc (7×100 mL). The combined ethyl acetate layer is washed with brine (50 mL), dried over sodium sulfate, and reduced in vacuo to give crude product which is purified by HPLC (C18 column) eluting with acetonitrile-water mixture to give 2-Pyridin-2-yl-pyrimidine-5-carboxylic acid ((S)-1-{3-[5-(1-hydroxy-1-methyl-ethyl)-1,2,4-oxadiazol-3-yl]-phenyl}-ethyl)-amide as amorphous glass (650 mg, 78%).

MS: 431 (M+H). ¹H NMR (300 MHz, DMSO): δ=1.58 (d, 3H), 1.62 (s, 6H), 5.3 (m, 1H), 7.56 (t, 1H), 7.7 (d, 1H), 7.92 (m, 2H), 8.08 (s, 1H), 8.43 (t, 1H), 8.72 (d, 1H), 8.9 (d, 1H), 9.47 (s, 2H), 9.59 (d, 1H).

[α]_d (Methanol)=+57.2°

Example 3

2-Pyridin-2-yl-pyrimidine-5-carboxylic acid ((R)-1-{3-[5-(1-hydroxy-1-methyl-ethyl)-1,2,4-oxadiazol-3-yl]-phenyl}-ethyl)-amide

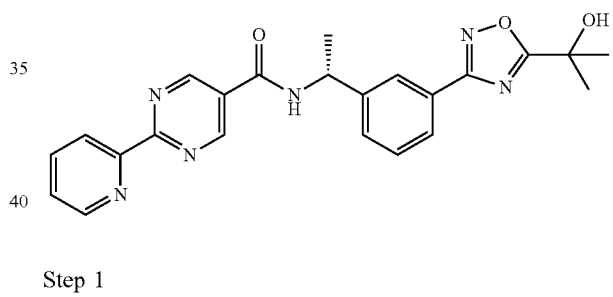

Step 1

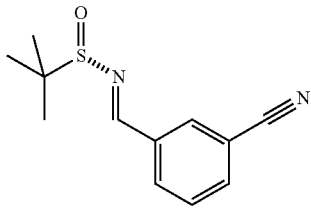

Potassium hydrogen sulfate (13.6 g, 100 mmol) is added to a mixture of 3-Formylbenzonitrile (7.21 g, 55 mmol) and (S)-(+)-2-Methyl-2-propanesulfinamide (6.06 g, 50 mmol) in toluene (500 mL) and heated at 45° C. for 2 days. The reaction mixture is filtered, the filtrate evaporated under reduced pressure and purified by column chromatography eluting with ethyl acetate-heptane mixture to give, N-[(3-cyanophenyl)methylene]-2-methyl-. [S(S)]-2-Propanesulfinamide (9.65 g)

MS: 235 (M+H). ¹H NMR (300 MHz, CDCl₃): δ=1.29 (s, 91H), 7.62 (t, 1H), 7.79 (d, 1H), 8.04 (d, 1H), 8.17 (bs, 1H), 8.60 (s, 1H).

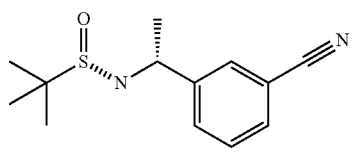

Methyl magnesium bromide (34.3 mL of 3M solution in diethyl ether, 102.9 mmol) is added over 30 minutes to a solution of N-[(3-cyanophenyl)methylene]-2-methyl-,[S(S)]-2-Propanesulfinamide (9.65 g, 41.18 mmol) in DCM (200 mL) at −45° C. and stirred at that temperature for 4 hrs. The cooling bath is then removed, allowed to warm up to −10° C. and quenched with saturated NaHCO$_3$ (250 mL). The organic layer is separated and the aqueous layer is extracted with more DCM (100 mL). The organic extracts are combined, dried (Na$_2$SO$_4$) and evaporated under reduced pressure to give 2-Methyl-propane-2-sulfinic acid [(R)-1-(3-cyano-phenyl)-ethyl]-amide as the major product.

MS: 251 (M+H).

$^1$H NMR (300 MHz, CDCl$_3$): δ=1.22 (s, 9H), 1.54 (d, 3H), 3.35 (s, 1H), 4.56-4.65 (m, 1H), 7.42-7.48 (m, 1H), 7.56-7.59 (m, 2H), 7.64 (s, 1H).

Step 3

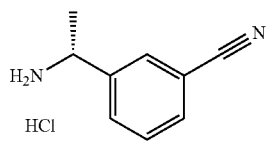

Hydrogen chloride (4N in p-dioxane, 21 mL) is added to a solution of 2-Methyl-propane-2-sulfinic acid [(R)-1-(3-cyano-phenyl)-ethyl]-amide (10.29 g, 41.1 mmol) in methanol (21 mL) and stirred at room temperature for 40 minutes. Reaction mixture is then evaporated under reduced pressure and the crude triturated with diethyl ether to give an off white solid which is crystallized from Methyl t-butyl ether and ethanol mixture to give 3-((R)-1-Amino-ethyl)-benzonitrile hydrochloride as the major product.

MS: 147 (M+H).

$^1$H NMR (300 MHz, DMSO): δ=1.53 (d, 3H), 4.45-4.52 (m, 1H), 7.65 (t, 1H), 7.84-7.91 (m, 2H), 8.03 (s, 1H), 8.67 (bs, 3H).

Step 4

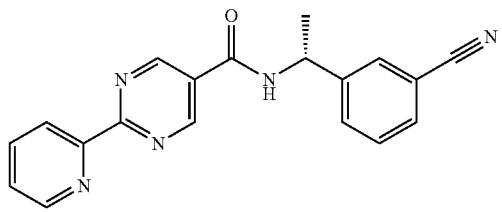 [SMILES: C[C@@H](NC(=O)c1cnc(-c2ccccn2)nc1)c1cccc(C#N)c1]

N-methyl morpholine (NMM) (1.01 g, 10 mmol) is added to a mixture of 2-Pyridin-2-yl-pyrimidine-5-carboxylic acid (2 g, 10 mmol) and 3-((R)-1-Amino-ethyl)-benzonitrile hydrochloride (1.82 g, 10 mmol) in DMF (50 mL). After stirring at room temperature for 10 minutes, 4-(4,6-Dimethoxy-[1,3,5]triazin-2-yl)-4-methyl-morpholin-4-ium chloride (DMTMM) (10 mmol) is added and the reaction stirred overnight at room temperature. The reaction mixture is partitioned between water (500 mL) and ethyl acetate (300 mL) and the aqueous layer is extracted with more ethyl acetate (100 mL). Combined ethyl acetate extracts is washed with saturated NaHCO3 (100 mL), and brine (100 mL). The organic layer is dried (Na$_2$SO$_4$), filtered and then evaporated under reduced pressure to give 2-Pyridin-2-yl-pyrimidine-5-carboxylic acid [(R)-1-(3-cyano-phenyl)-ethyl]-amide as the major product (3.2 g) which is taken directly into the next reaction (amidoxime formation).

Step 5

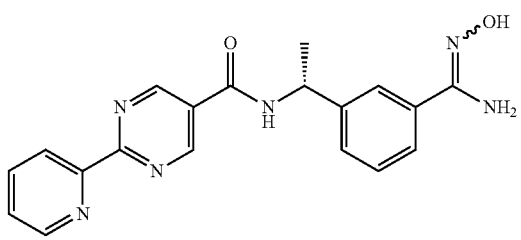 [SMILES: C[C@@H](NC(=O)c1cnc(-c2ccccn2)nc1)c1cccc(C(N)=NO)c1]

Hydroxylamine hydrochloride (1.52 g, 24.2 mmol) is added to a cooled solution of 2-Pyridin-2-yl-pyrimidine-5-carboxylic acid [(R)-1-(3-cyano-phenyl)-ethyl]-amide (3.2 g, 9.7 mmol) in methanol (40 mL) and the suspension cooled in an ice water bath. Triethyl amine (2.44 g, 24.2 mmol) is added to the flask and the reaction mixture is allowed to warm to room temperature over night. The reaction mixture evaporated under reduced pressure and the crude partitioned between water and ethyl acetate. Organic layer is separated, dried (Na$_2$SO$_4$) and evaporated under reduced pressure. Toluene (50 mL) and CHCl$_3$ (50 mL) are added and evaporated under reduced pressure to give 2-Pyridin-2-yl-pyrimidine-5-carboxylic acid {(R)-1-[3-(N-hydroxycarbamimidoyl)-phenyl]-ethyl}-amide (3 g) as the major product.

MS: 363 (M+H).

$^1$H NMR (300 MHz, DMSO): δ=1.54 (d, 3H), 5.18-5.27 (m, 1H), 5.80 (bs, 2H), 7.35 (t, 1H), 7.44 (d, 1H), 7.54-7.60 (m, 2H), 7.74 (s, 1H), 8.45 (d, 1H), 8.79 (d, 1H), 9.26 (d, 1H), 9.35 (s, 2H), 9.60 (s, 1H).

Step 6

2-Pyridin-2-yl-pyrimidine-5-carboxylic acid ((R)-1-{3-[5-(1-hydroxy-1-methyl-ethyl)-1,2,4-oxadiazol-3-yl]-phenyl}-ethyl)-amide Methyl 2-hydroxy-2-methyl-propionate (2 mL) and K$_2$CO$_3$ (219 mg, 1.59 mmol) are added to a microwave vial containing 2-Pyridin-2-yl-pyrimidine-5-carboxylic acid {(R)-1-[3-(N-hydroxycarbamimidoyl)-phenyl]-ethyl}-amide (0.5 g, 1.38 mmol) and heated at 180° C. in a microwave for 10 minutes. The reaction mixture is evaporated under reduced pressure and purified by reverse phase HPLC to give 2-Pyridin-2-yl-pyrimidine-5-carboxylic acid ((R)-1-{3-[5-(1-hydroxy-1-methyl-ethyl)-1,2,4-oxadiazol-3-yl]-phenyl}-ethyl)-amide as the major compound (110 mg).

MS: 431 (M+H).

$^1$H NMR (300 MHz, DMSO): δ=1.58 (d, 3H), 1.61 (s, 6H), 5.27-5.31 (m, 1H), 6.08 (s, 1H), 7.53-7.60 (m, 2H), 7.67 (d, 1H), 7.91 (d, 1H), 8.02 (t, 1H), 8.08 (s, 1H), 8.45 (d, 1H), 8.79 (d, 1H), 9.35-9.39 (m, 3H).

2-Pyridin-2-yl-pyrimidine-5-carboxylic acid ((R)-1-{3-[5-(1-hydroxy-1-methyl-ethyl)-1,2,4-oxadiazol-3-yl]-phenyl}-ethyl)-amide can also be prepared by following procedures similar to those of Example 2 but substituting 2-{3-

[3-((R)-1-Amino-ethyl)-phenyl]-1,2,4-oxadiazol-5-yl}-propan-2-ol Hydrochloride for 2-(3-[3-((S)-1-Amino-ethyl)-phenyl]-1,2,4-oxadiazol-5-yl-propan-2-ol Hydrochloride.

In Vitro Assay Protocols to Identify Inhibitors of Hematopoietic PGD2 Synthase

The compounds of the present invention can be tested for enzymatic inhibiting activity against PGD2 Synthase according to either one of the following assays.
Assay 1: Fluorescence Polarization Assay As described in PCT publication WO 2004/016223, Example II.
Assay 2: Enzyme Immunoassay (EIA) method
I. Assay Solutions
  a. Preparation of 0.1M $K_2HPO_4/KH_2PO_4$ buffer (pH 7.4)
    Prepare 0.1 M $KH_2PO_4$ from 1M $KH_2PO_4$ (Sigma, Cat# P-8709)
    Prepare 0.1 M $K_2HPO_4$ from powder of $K_2HPO_4$ (Fisher, BP363-500)
    Mix 0.1 M $K_2HPO_4$ with 0.1 M $KH_2PO_4$ to adjust pH to 7.4.
  b. Preparation of 0.5% γ-globulin
    Add 0.1 g of γ-globulin (Sigma, Cat# G-5009) to 20 mL 0.1 M $K_2HPO_4/KH_2PO_4$ buffer (pH 7.4) and make 1-mL/vial aliquots and store in −80° C.
  c. Preparation of 100 mM GSH
    Add 307 mg of GSH (Sigma, Cat# G-6529) to 10 mL 0.1 M $K_2HPO_4/KH_2PO_4$ buffer (pH 7.4) and store at −80° C.
  d. Preparation of Reaction buffer:
    198 mL of 0.1M $K_2HPO_4/KH_2PO_4$ buffer (pH 7.4)
    2 mM GSH—Prepared from 100 mM GSH
    0.4 g Glycerol
    2 mL of 0.5% γ-globulin
    Add 0.4 g of glycerol and 2 mL of 0.5% γ-globulin to 198 mL of 0.1 M $K_2HPO_4/KH_2PO_4$, buffer (pH7.4).
    Add 0.4 mL of 100 mM GSH to 19.6 mL reaction buffer before the assay (enough for two 96-well plates).
  e. Preparation of $FeCl_2$/citric acid stopping solution: (8 mg/mL $FeCl_2$, 0.1 M citric acid)
    Add 40 mg fresh $FeCl_2$ (IGN, Cat#158046) to 5 mL 0.1 M citric acid (Sigma, Cat#C0759).
  f. Preparation of MOX reagent:
    10% EtOH—Add 1 mL of EtOH to 9 mL of ultra pure $H_2O$
    Dissolve 0.1 g of methoxylamine (Cayman, Cat#400036/) in 10% EtOH (10 mL).
    Add 0.82 g of sodium acetate (Cayman, Cat#400037) to MOX solution and dissolve.
II. Materials and Method
  Dimethylsulfoxide (DMSO; Sigma; Cat# D2650)
  Prostaglandin D2-MOX express EIA kit (Caymen Chemical, Catalog No. 500151)
  Before the assay, cool down 10 mL of acetone in polypropylene tubes and empty 96 well plates in ice. All the procedures except compound dilution are performed on ice.
III. Compound Dilution
  1. Dilute compound in DMSO

| Vol of DMSO stock solution (μL) | DMSO (μL) | Compound concentration (mM) |
|---|---|---|
| 4 μL of 10 mM | 6 μL | 4 |
| 3 μL of 4 mM | 6 μL | 1.3333 |
| 3 μL of 1.33 mM | 6 μL | 0.4444 |
| 3 μL of 0.44 mM | 6 μL | 0.1481 |
| 3 μL of 0.148 mM | 6 μL | 0.0494 |
| 3 μL of 0.049 mM | 6 μL | 0.0165 |
| 3 μL of 0.016 mM | 6 μL | 0.0055 |

2. Dilute 2 L of each above concentration of compound to 38 μL of reaction buffer in 96-well plates and mix.
IV. Enzyme and Substrate Solution Preparation
  1. Preparation of 0.39 ng/μL enzyme solution (0.35 ng/μL at final after compound addition).
    Mix 4 μL of 4 mg/mL human h-PGDS with 396 μL of reaction buffer (to give enzyme concentration 40 μg/mL). Add 46.8 μL of 40 μg/mL h-PGDS to 4.753 mL of reaction buffer to give a total volume of 4.8 mL
  2. Preparation of Substrate Solution (PGH2): Add 0.375 mL of 0.1 mg/mL of PGH2 to 1.625 mL acetone.
V. Enzyme reaction:
  1. Add 60 μL of enzyme solution to compound well and positive control (without compound) in U-bottom polypropylene plate on ice.
  2. Add 60 μL of reaction buffer and 6.6 μL of 5% DMSO in reaction buffer into negative control wells in the plate.
  3. Add 6.6 μL of diluted compound in reaction buffer to the compound wells and mix.
  4. Add 6.6 μL of 5% DMSO in reaction buffer to the positive control well.
  5. Incubate the plate in ice for at least 30 min.
  6. Add 20 μL of substrate (PGH2) solution to compound, negative and positive control wells in the U-bottom 96 well plate on ice.
  7. Dry the plate in cold room for about 25-28 min.
  8. Pipette 45 μL of enzyme solution (above) into 96-wells with dried PGH2 and mix 3 times. Incubate on the ice for 1 min.
  9. Add 45 μL of $FeCl_2$ solution into each wells and mix.
  10. Add 90 μL of MOX solution and mix.
  11. Incubate for 30 min at 60° C.
  12. Dilute the samples 2500× with EIA buffer.
VI. EIA Assay
  Perform the assay according to the procedure in EIA kit provided by Cayman. Total PGD2 levels (pg/mL) were determined in the samples by EIA kits (Cayman Chemical, Catalog No. 500151)
Calculate amount of PGD2 as below
Calculated % Positive control according to the equation below;

% Positive control=(Compound value-Negative control)/(Positive value-Negative control value)×100.

$$\% \text{ Positive control} = \frac{(\text{Compound value} - \text{Negative control})}{(\text{Positive value} - \text{Negative control value})} \times 100$$

Compound value=PGD2 levels (pg/mL) obtained from the standard curve in EIA assay for the samples with compound Negative control value=PGD2 levels (pg/mL) obtained from the standard curve in EIA assay for the samples without enzyme
Positive control value=PGD2 levels (pg/mL) obtained from the standard curve in EIA assay for the samples with enzyme but without compound
$IC_{50}$s are determined by excel fit to get the x value when y=1/2 Ymax using 4 parameter logistic model for the $IC_{50}$ curves.

Results

Compounds within the scope of the invention produce 50% inhibition in the Fluorescence Polarization Assay or the EIA assay at concentrations within the range of about 1 nanomolar to about 30 micromolar, particularly about 1 nanomolar to about 1 micromolar, and more particularly about 1 nanomolar to about 100 nanomolar.

| Example | hPGDS EIA IC50 nM | solidsol μM |
|---|---|---|
| 1 | 12 | 135.9 |
| 2 | 11 | 854.9 |
| 3 | 26 | 29.4 |

The present invention may be embodied in other specific forms without departing from the spirit or essential attributes thereof.

We claim:

1. A pharmaceutical composition comprising 2-pyridin-2-yl-pyrimidine-5-carboxylic acid 3-[5-(1-hydroxy-1-methyl-ethyl)-1,2,4-oxadiazol-3-yl]-benzylamide and a pharmaceutically acceptable carrier.

2. A pharmaceutical composition comprising a pharmaceutically acceptable salt of 2-pyridin-2-yl-pyrimidine-5-carboxylic acid 3-[5-(1-hydroxy-1-methyl-ethyl)-1,2,4-oxadiazol-3-yl]-benzylamide and a pharmaceutically acceptable carrier.

3. A method for treating an allergic or inflammatory disorder in a patient in need thereof, wherein the allergic or inflammatory disorder is selected from the group consisting of allergic rhinitis, asthma, and chronic obstructive pulmonary disease, the method comprising administering to the patient a pharmaceutically effective amount of 2-pyridin-2-yl-pyrimidine-5-carboxylic acid 3-[5-(1-hydroxy-1-methyl-ethyl)-1,2,4-oxadiazol-3-yl]-benzylamide.

4. The method of claim 3, wherein the allergic or inflammatory disorder is asthma.

5. The method of claim 3, wherein the allergic or inflammatory disorder is chronic obstructive pulmonary disease.

6. A method for treating an allergic or inflammatory disorder in a patient in need thereof, wherein the allergic or inflammatory disorder is selected from the group consisting of allergic rhinitis, asthma, and chronic obstructive pulmonary disease, the method comprising administering to the patient a pharmaceutically effective amount of a pharmaceutically acceptable salt of 2-pyridin-2-yl-pyrimidine-5-carboxylic acid 3-[5-(1-hydroxy-1-methyl-ethyl)-1,2,4-oxadiazol-3-yl]-benzylamide.

7. The method of claim 6, wherein the allergic or inflammatory disorder is asthma.

8. The method of claim 6, wherein the allergic or inflammatory disorder is chronic obstructive pulmonary disease.

* * * * *